US007601352B1

(12) United States Patent
Novak (10) Patent No.: US 7,601,352 B1
(45) Date of Patent: Oct. 13, 2009

(54) MONOCLONAL ANTIBODIES AND ANTIGEN BINDING FRAGMENTS THEREOF CAPABLE OF BINDING TRKA AND INHIBITING THE FUNCTIONAL ACTIVATION OF TRKA

(75) Inventor: Michal M. Novak, Bratislava (SK)

(73) Assignee: Lay Line Genomics S.p.A., Rome (IT)

( * ) Notice: Subject to any disclaimer, the term of this patent is extended or adjusted under 35 U.S.C. 154(b) by 0 days.

(21) Appl. No.: 09/979,710

(22) PCT Filed: May 26, 2000

(86) PCT No.: PCT/IT00/00218

§ 371 (c)(1),
(2), (4) Date: Mar. 8, 2002

(87) PCT Pub. No.: WO00/73344

PCT Pub. Date: Dec. 7, 2000

(30) Foreign Application Priority Data

May 26, 1999 (IT) .............................. RM99A0333

(51) Int. Cl.
*A61K 39/395* (2006.01)
*A61K 39/00* (2006.01)
(52) U.S. Cl. .............. 424/141.1; 424/142.1; 424/135.1; 424/136.1; 424/130.1; 530/388.1; 530/388.22
(58) Field of Classification Search ........................ None
See application file for complete search history.

(56) References Cited

FOREIGN PATENT DOCUMENTS

| DE | DD296964 | * | 12/1991 |
|---|---|---|---|
| EP | 0 471 205 A1 | | 2/1992 |
| WO | WO 95/15180 | | 6/1995 |
| WO | WO9710354 | * | 3/1997 |

OTHER PUBLICATIONS

Rudikoff et al. Proc Natl. Acad. Sci. USA 1982 vol. 79: p. 1979.*
Kramer et al. Eur J. Cancer 1997. 33: 2090-91.*
Hudson et al. J. Immunol. Method. 1999. 231:177-189.*
Peterson et al. DNA and Cell Biol. 1998. 17: 1031-1040.*
Gomi et al. Proc. Natl. Acad. Sci. USA. 1994. 91: 2824-2828.*
Urfer et al. J. Biol. Chem. 1998. 273:5829-5840.*
Debeir et al., "A nerve growth factor mimetic TrkA antagonist causes withdrawal of cortical cholinergic boutons in the adult rat.", Proceedings of the National Academy of Sciences of the United States of America, vol. 96 pp. 4067-4072 (1999).
LeSauteur et al., "Potent Human P140-TrkA Agonists Derived from an Anti-receptor Monoclonal Antibody", Journal of Neuroscience, U.S., New York, NY., vol. 16, No. 4, pp. 1308-1316 (1996).
Cattaneo et al., "Functional blockade of tyrosine kinase A in the rat basal forebrain by a novel antagonistic anti-receptor monoclonal antibody.", Journal of Neuroscience, vol. 19, No. 22, pp. 9687-9697, (1999).
Camoratto, et al., "CEP-751 Inhibits TRK Receptor Tyrosine Kinase Activity in vitro and Exhibits Anti-Tumor Activity," Int. J. Cancer (1997), vol. 72, pp. 673-679.
Cattaneo, et al., "Functional Blockade of Tyrosine Kinase A in the Rat Basal Forebrain by a Novel Antagonistic Anti-Receptor Monoclonal Antibody," The Journal of Neuroscience (1999), vol. 19(22), pp. 9687-9697.
Chen, et al., "A Chemical-Genetic Approach to Studying Neurotrophin Signaling," Neuron (2005), vol. 46, pp. 13-21.
Clary, et al., "TrkA Cross-linking Mimics Neuronal Responses to Nerve Growth Factor," Molecular Biology of the Cell (1994), vol. 5, pp. 549-563.
Coulier, et al., "Human trk Oncogenes Activated by Point Mutation, In-Frame Deletion, and Duplication of the Tyrosine Kinase Domain," Molecular and Cellular Biology (1990), vol. 10, pp. 4202-4210.
Covaceuszach, et al., "Neutralilzation of NGF-TrkA Receptor Interaction by the Novel Antagonistic Anti-TrkA Monoclonal Antibody MNAC13: A Structural Insight," Proteins: Structure, Function, and Bioinformatics (2005), vol. 58, pp. 717-727.
Cunningham and Greene, "A function-structure model for NGF-activated TRK," The EMBO Journal (1998), vol. 17, No. 24, pp. 7282-7293.
Hempstead, et al, "Overexpression of the trk Tyrosone Kinase Rapidly Accelerates Nerve Growth Factor-Induced Differentiation," Neuron (1992), vol. 9, pp. 883-896.
Hongo, et al., "Development and Characterization of Novel TRK—a Specific Monoclonal Antibodies," Society for Neuroscience (1996), vol. 22, p. 1010.
Hongo, et al., "Development and Characterization of Murine Monoclonal Antibodies to the Latency-Associated Peptide of Transforming Growth Factor $\beta_1$," Hybridoma (1995), vol. 14, No. 3, pp. 253-260.
Inagaki, et al., "TrkA Tyrosine Residues Involved in NGF-induced Neurite Outgrowth of PC12 Cells", European Journal of Neuroscience (1995), vol. 7, pp. 1125-1133.
Klesse, et al., "Nerve growth factor induces survival and differentiation through two distinct signaling cascades in PC12 cells," Oncogene (1999), vol. 18, pp. 2055-2068.
Lee and Chao, "Activation of Trk neurotrophin receptors in the absence of neurotrophins," Proc. Natl. Acad. Sci. (2001), vol. 98, No. 6, pp. 3555-3560.
Minichiello, et al., "Mechanisms of TrkB-Mediated Hippocampal Long-Term Potentiation," Neuron (2002), vol. 36, pp. 121-137.
Oskam, et al., "Frequent generation of oncogenes by in vitro recombination of TRK protooncogene sequences," Proc. Natl. Acad. Sci. USA (1988), vol. 85, pp. 2964-2968.
Pesavento, et al., "Blocking the NGF-TrkA Interaction Rescues the Developmental Loss of LTP in the Rat Visual Cortex: Rose of the Cholinergic System," Neuron (2000), vol. 25, pp. 165-175.

(Continued)

*Primary Examiner*—Christine J Saoud
*Assistant Examiner*—Chang-Yu Wang
(74) *Attorney, Agent, or Firm*—Edwards Angell Palmer & Dodge LLP; Peter C. Lauro, Esq.

(57) ABSTRACT

Monoclonal antibodies, synthetic and biotechnological derivatives thereof (ScFv or others) are able to recognize the NGF high affinity receptor, TrkA, and act as NGF-antagonist molecules. Pharmacological compositions for therapy, gene therapy, diagnostics of neurological pathologies are also described. Transgenic animal models to study such pathologies are also described.

12 Claims, 8 Drawing Sheets

OTHER PUBLICATIONS

Rakhit, et al., "Nerve Growth Factor Stimulation of p42/p44 Mitogen-Activated Protein Kinase in PC12 Cells: Role of $G_{i/o}$, G Protein-Coupled Receptor Kinase 2, β-Arrestin I, and Endocytic Processing," Molecular Pharmacology (2001), vol. 60, pp. 63-70.

Rende, et al., "Nerve growth factor (NGF) influences differentiation and proliferation of myogenic cells in vitro via TrKA," Int. J. Devl Neuroscience (2000), vol. 18, pp. 869-885.

Sadick, et al., "Analysis of Neurotrophim/Receptor Interactions with a gD-Flag-Modified Quantitative Kinase Receptor Activation (gD. KIRA) Enzyme-Linked Immunosorbent Assay," Experimental Cell Research (1997), vol. 234, pp. 354-361.

Sadick, et al., "Analysis of Heregulin-Induced ErbB2 Phosphorylation with a High-Throughput Kinase Receptor Activation Enzyme-Linked Immunosorbant Assay," Analytical Biochemistry (1996), vol. 235, pp. 207-214.

Urfer, et al., "High Resolution Mapping of the Binding Site of TrkA for Nerve Growth Factor and TrkC for Neurotrophin-3 on the Second Immunoglobulin-like Domain of the Trk Receptors," The Journal of Biological Chemistry (1998), vol. 273, pp. 5829-5840.

Xiao, et al., "Variant PC12 Cell Line That Spontaneously Differentiates and Extends Neuritic Processes," Journal of Neuroscience Research (2002), vol. 69, pp. 104-109.

Zola, Monoclonal Antibodies, CRC Press, Inc., Boca Raton, FL (1987).

Definition of "antagonist" from On-line Medical Dictionary, Nov. 18, 1997, http://cancerweb.ncl.ac.uk/cgi-bin/omd?query=antagonist&action=Search+OMD, Published at the Centre for Cancer Education, University of Newcastle upon Tyne, The CancerWEB Project, copyright 1997-2005.

Bedian, Vahe, Declaration regarding European Patent No. 1181318 in the name of Lay Line Genomics SpA, pp. 1-3, dated Jul. 2, 2009.

Benigni, Fabio, "Declaration of Dr. Fabio Benigni," regarding European Patent No. 1181318 in the name of Lay Line Genomics SpA, pp. 1-22, submitted Jul. 3, 2009.

Thress, Kenneth, Declaration regarding European Patent No. 1181318 in the name of Lay Line Genomics SpA, dated Jun. 26, 2009.

* cited by examiner

SEQUENCE LISTING

```
<160> NUMBER OF SEQ ID NOS: 2

<210> SEQ ID NO 1
<211> LENGTH: 888
<212> TYPE: DNA
<213> ORGANISM: human ScFv antibody
<220> FEATURE:
<221> NAME/KEY: CDS
<222> LOCATION: (1)..(888)

<400> SEQUENCE: 1 atg aaa tac cta ttg cct acg gca gcc gct gga ttg tta tta ctc gca        48
Met Lys Tyr Leu Leu Pro Thr Ala Ala Ala Gly Leu Leu Leu Leu Ala
 1               5                  10                  15 gca agc ggc gcg cat gcc gat att gtt ctc tcc cag tct cca gca atc        96
Ala Ser Gly Ala His Ala Asp Ile Val Leu Ser Gln Ser Pro Ala Ile
             20                  25                  30 atg tct gca tct cta ggg gag gag atc acc cta acc tgc agt gcc agc       144
Met Ser Ala Ser Leu Gly Glu Glu Ile Thr Leu Thr Cys Ser Ala Ser
         35                  40                  45 tcg agt gta agt tac atg cac tgg tac cag cag aag tca ggc act tct       192
Ser Ser Val Ser Tyr Met His Trp Tyr Gln Gln Lys Ser Gly Thr Ser
     50                  55                  60 ccc aag ctc ttg att tat act aca tcc aac ctg gct tct gga gtc cct       240
Pro Lys Leu Leu Ile Tyr Thr Thr Ser Asn Leu Ala Ser Gly Val Pro
 65                  70                  75                  80 tct cgc ttc agt ggc agt ggg tct ggg acc ttt tat tct ctc aca atc       288
Ser Arg Phe Ser Gly Ser Gly Ser Gly Thr Phe Tyr Ser Leu Thr Ile
                 85                  90                  95
```

```
agt agt gtg gag gct gaa gat gct gcc gat tat tac tgc cat cag tgg    336
Ser Ser Val Glu Ala Glu Asp Ala Ala Asp Tyr Tyr Cys His Gln Trp
            100                 105                 110 agt agt tat cca tgg acg ttc ggt gga ggc acc aag ctg gaa atc aaa    384
Ser Ser Tyr Pro Trp Thr Phe Gly Gly Gly Thr Lys Leu Glu Ile Lys
        115                 120                 125 cgt tcc gga ggg tcg acc ata act tcg tat aat gta tat tat acg aag    432
Arg Ser Gly Gly Ser Thr Ile Thr Ser Tyr Asn Val Tyr Tyr Thr Lys
130                 135                 140 tta tcc tcg agc ggt acc gag gtg aag ctg atg gag tct ggg gga ggt    480
Leu Ser Ser Ser Gly Thr Glu Val Lys Leu Met Glu Ser Gly Gly Gly
145                 150                 155                 160 tta gtg cag cct gga ggg tcc ctg aaa ctc tcc tgt gca gcc tct gga    528
Leu Val Gln Pro Gly Gly Ser Leu Lys Leu Ser Cys Ala Ala Ser Gly
                165                 170                 175 ttc act ttc agt acc tat acc atg tct tgg gct cgc cag act cca gag    576
Phe Thr Phe Ser Thr Tyr Thr Met Ser Trp Ala Arg Gln Thr Pro Glu
            180                 185                 190 aag agg ctg gag tgg gtc gca tac att agt aaa ggt ggt ggt agt acc    624
Lys Arg Leu Glu Trp Val Ala Tyr Ile Ser Lys Gly Gly Gly Ser Thr
        195                 200                 205 tac tat cca gac act gta aag ggc cga ttc acc atc tcc agg gac aat    672
Tyr Tyr Pro Asp Thr Val Lys Gly Arg Phe Thr Ile Ser Arg Asp Asn
210                 215                 220 gcc aag aac acc ctg tac ctg caa atg agc agt ctg aag tct gag gac    720
Ala Lys Asn Thr Leu Tyr Leu Gln Met Ser Ser Leu Lys Ser Glu Asp
225                 230                 235                 240 acg gcc ttg tat tac tgt gca aga ggg gct atg tat ggt aac gat ttt    768
Thr Ala Leu Tyr Tyr Cys Ala Arg Gly Ala Met Tyr Gly Asn Asp Phe
                245                 250                 255 ttc tat cct atg gac tac tgg ggt caa gga acc tca gtc acc gtc tcc    816
Phe Tyr Pro Met Asp Tyr Trp Gly Gln Gly Thr Ser Val Thr Val Ser
            260                 265                 270 tca gct agc ggc aaa cca atc cca aac cca ctg ctg ggc ctg gat agt    864
Ser Ala Ser Gly Lys Pro Ile Pro Asn Pro Leu Leu Gly Leu Asp Ser
        275                 280                 285 act cac cat cac cat cac cat tag                                    888
Thr His His His His His His
    290                 295

<210> SEQ ID NO 2
<211> LENGTH: 295
<212> TYPE: PRT
<213> ORGANISM: human ScFv antibody

<400> SEQUENCE: 2

Met Lys Tyr Leu Leu Pro Thr Ala Ala Ala Gly Leu Leu Leu Leu Ala
 1               5                  10                  15

Ala Ser Gly Ala His Ala Asp Ile Val Leu Ser Gln Ser Pro Ala Ile
                20                  25                  30

Met Ser Ala Ser Leu Gly Glu Glu Ile Thr Leu Thr Cys Ser Ala Ser
            35                  40                  45

Ser Ser Val Ser Tyr Met His Trp Tyr Gln Gln Lys Ser Gly Thr Ser
        50                  55                  60

Pro Lys Leu Leu Ile Tyr Thr Thr Ser Asn Leu Ala Ser Gly Val Pro
65                  70                  75                  80

Ser Arg Phe Ser Gly Ser Gly Ser Gly Thr Phe Tyr Ser Leu Thr Ile
                85                  90                  95
```

-continued

| | | | | | | | | | | | | |
|---|---|---|---|---|---|---|---|---|---|---|---|---|
| Ser | Ser | Val | Glu | Ala | Glu | Asp | Ala | Ala | Asp | Tyr | Tyr | Cys | His | Gln | Trp |
| | | | 100 | | | | 105 | | | | | 110 | | | |
| Ser | Ser | Tyr | Pro | Trp | Thr | Phe | Gly | Gly | Thr | Lys | Leu | Glu | Ile | Lys |
| | | 115 | | | | 120 | | | | | 125 | | | |
| Arg | Ser | Gly | Gly | Ser | Thr | Ile | Thr | Ser | Tyr | Asn | Val | Tyr | Tyr | Thr | Lys |
| | 130 | | | | | 135 | | | | | 140 | | | | |
| Leu | Ser | Ser | Ser | Gly | Thr | Glu | Val | Lys | Leu | Met | Glu | Ser | Gly | Gly | Gly |
| 145 | | | | | 150 | | | | | 155 | | | | | 160 |
| Leu | Val | Gln | Pro | Gly | Gly | Ser | Leu | Lys | Leu | Ser | Cys | Ala | Ala | Ser | Gly |
| | | | | 165 | | | | | 170 | | | | | 175 | |
| Phe | Thr | Phe | Ser | Thr | Tyr | Thr | Met | Ser | Trp | Ala | Arg | Gln | Thr | Pro | Glu |
| | | | 180 | | | | | 185 | | | | | 190 | | |
| Lys | Arg | Leu | Glu | Trp | Val | Ala | Tyr | Ile | Ser | Lys | Gly | Gly | Gly | Ser | Thr |
| | | | 195 | | | | | 200 | | | | | 205 | | |
| Tyr | Tyr | Pro | Asp | Thr | Val | Lys | Gly | Arg | Phe | Thr | Ile | Ser | Arg | Asp | Asn |
| | | 210 | | | | | 215 | | | | | 220 | | | |
| Ala | Lys | Asn | Thr | Leu | Tyr | Leu | Gln | Met | Ser | Ser | Leu | Lys | Ser | Glu | Asp |
| 225 | | | | | 230 | | | | | 235 | | | | | 240 |
| Thr | Ala | Leu | Tyr | Tyr | Cys | Ala | Arg | Gly | Ala | Met | Tyr | Gly | Asn | Asp | Phe |
| | | | | 245 | | | | | 250 | | | | | 255 | |
| Phe | Tyr | Pro | Met | Asp | Tyr | Trp | Gly | Gln | Gly | Thr | Ser | Val | Thr | Val | Ser |
| | | | 260 | | | | | 265 | | | | | 270 | | |
| Ser | Ala | Ser | Gly | Lys | Pro | Ile | Pro | Asn | Pro | Leu | Leu | Gly | Leu | Asp | Ser |
| | | 275 | | | | | 280 | | | | | 285 | | | |
| Thr | His | His | His | His | His |
| | 290 | | | | 295 |

MONOCLONAL ANTIBODIES AND ANTIGEN BINDING FRAGMENTS THEREOF CAPABLE OF BINDING TRKA AND INHIBITING THE FUNCTIONAL ACTIVATION OF TRKA

The present invention relates to monoclonal antibodies, to synthetic and biotechnological derivatives thereof, acting as NGF-antagonist molecules.

More particularly the invention relates to a monoclonal antibody, to synthetic and recombinant derivatives thereof able to recognise and bind the high affinity tyrosine kinase receptor of NGF (Nerve Growth Factor), named as TrkA, and act as antagonist for the binding of NGF to TrkA. The invention also concerns diagnostic and therapeutic uses of such molecules, and related compositions.

Neurotrophins are a family of peptide growth factors (Barde, 1994), structurally related to the first member of the family, NGF (Nerve Growth Factor, Levi-Montalicini, 1987). Neurotrophins modulate neuronal differentiation and survival, as well the synaptic transmission, both of peripheral neurons and of the central nervous system. Furthermore NGF acts on various non neuronal tissues and cells, as immune system cells.

NGF acts through two membrane receptors present in the target cells, the low affinity p75 receptor, and the 140 kDa high affinity transmembrane glycoprotein, TrkA (Kaplan et al., 1991, Klein et al., 1991) having a tyrosine kinase activity. TrkA is expressed in neural-crest neurons, in sympathetic neurons as well as in cholinergic neurons of the basal forebrain and corpus striatum, where it represents the crucial mediator of NGF activities (Holtzman et al., 1992; Verge et al., 1992). TrkA is also expressed in some non neuronal tissues and cells, including B lymphocytes (Torcia et al., 1996).

Prior art suggests the potential use of NGF for the treatment of various neurodegenerative pathologies, including Alzheimer's disease (Lindsay et al., 1994; Ebendal et al., 1991), and other pathologies, as diabetes mellitus and leprosy (Anand et al., 1996). However initial clinical tests were discouraging, complicated by delivery difficulties, by the pharmacokinetics in the central nervous system, and by NGF negative agonist properties towards other peripheral targets, out of the central nervous system, which lead to excessive and undesired stimuli.

Therefore there is the need to develop antagonist molecules selective for the interaction NGF-TrkA receptor and pharmacologically active derivatives thereof, which are easily delivered.

Furthermore, the NGF over-production in various inflammatory conditions was related to the increase of pain sensitivity of the primary afferent nociceptors, thus contributing to the occurrence of a chronic pain condition. The population of sensorial neurons that are sensitive to tissue damages (nociceptors) is particularly NGF-dependent. In addition, considering the disadvantages and limitations of the two existing analgesic drug classes (non steroidal anti-inflammatory drugs and opiates), the provision of a new different target, as NGF, represents a progress in the art (Snider and McMahon, 1998). And further, as suggested by Levine (Levine, 1998) NGF provides a potential target for the design of new therapies of the pain, specially those resulting from inflammatory or neuropathic conditions, for which conventional drugs are less effective. Finally new studies showed a direct relation between pain and TrkA system demonstrating, in four unrelated cases of type 4 pain chronic insensitivity, with anhidrosis, the presence of mutations of the TrkA gene and consequently the absence of functional NGF receptors (Indo et al., 1996; Wood, 1996).

Accordingly the NGF-TrkA system provides a potential target to design pain therapies, i.e. treatments able to antagonise the pain neuropathic syndrome by means of TrkA-effective antagonists (Levine, 1998; Snider and Mcmahon, 1998).

The aberrant expression of the TrkA receptor mRNA was related also to neoplastic pathologies. The prognosis of TrkA expressing tumours, the "imaging" diagnostic and the therapy as well represent an application area of antibodies having an high affinity for TrkA. As a matter of fact, in these tumours TrkA binding agents represent useful tools of the clinical diagnosis, prognosis and therapeutic treatments (Kramer et al., 1997).

Recombinant antibodies (Vaughan et al., 1998) represent starting reagents of choice for the development of small molecule mimicking their activity (Le Sauteur et al., 1995).

A TrkA-agonist monoclonal antibody was described by Le Sauteur et al., 1996 and in PCT application No. WO97/21732. The agonist activity of the only disclosed antibody (5C3) makes it not suitable for the aims of the present invention and in all the situations wherein the hyper-activation of the TrkA receptor must be avoided. PCT application No. WO97/21732 discloses the use as "imaging" diagnostic of the agonist antibody 5C3. However this antibody, due to its agonist activity, can not be used for the above application, unless the receptor activation is not hampered.

Therefore it is clear the need for the development of new molecules suitable to interfere with the binding of NGF to TrkA, to provide new therapeutic activities and, particularly, to provide a TrkA antibody acting as antagonist and then ideal for blocking the receptor activation by endogenous ligand (NGF), and having no activation activity of the receptor. Furthermore the antibody could be advantageously used for the development of reagents, i.e. synthetic and recombinant fragments blocking the NGF-TrkA interaction.

The author of the present invention isolated various monoclonal antibodies able to interact with the NGF-receptor, named TrkA. Among these an antibody, named MNAC13, acts as a strong antagonist of TrkA, by inhibiting the binding of NGF to TrkA. This antibody represents a very effective tool in preventing the functional activation of TrkA by NGF in a variety of biological systems.

The antibody was derived by congenic immunization of Balb/C mice, with a human native TrkA receptor expressed on Balb/C 3T3 cells. The screening was based on the ability of the antibodies to inhibit the binding of NGF to TrkA-expressing cells. This led to the isolation of antibodies able to bind TrkA at its NGF-binding domain, thus preventing the binding of NGF. The antibody MNAC13 is very effective in preventing the functional activation of TrkA by NGF in different biological systems. The author of the present invention cloned also the genes enacoding the variable regions of the MNAC13 antibody and, by means of recombinant DNA techniques, assembled such regions in a functional polypeptide of reduced size (single chain Fv fragment, scFvMNAC13), confirming that it retains the properties of the parental antibody.

An agonist antibody means an antibody able to activate the receptor antigen in the absence of the native ligand of the receptor itself.

An antagonist antibody means an antibody directed against the active site of the antigen receptor and able to inhibit the activity of the natural ligand being in competition with the latter for binding to the receptor itself.

Synthetic and biotechnological derivatives of an antibody mean any engineered fragment, synthesised by chemical or recombinant techniques, which retain the functional properties of the antibody.

It is an object of the present invention a monoclonal antibody, synthetic and biotechnological derivatives thereof, able to recognise and bind the high affinity tyrosine kinase receptor of NGF (Nerve Growth Factor), named as TrkA, and act as antagonist for the binding of NGF to TrkA.

According to a preferred embodiment, the antibody of the invention has the light chain variable region essentially consisting of the sequence from aa. 23 to aa. 134 of SEQ ID No. 2.

According to a further preferred embodiment, the antibody of the invention has the heavy chain variable region essentially consisting of the sequence from aa. 152 to aa. 276 of SEQ ID No. 2

According to a further preferred embodiment the biotechnological derivative of the invention is a ScFv fragment comprising:

a) the light chain variable region of the antibody of the invention or functional derivatives thereof, and b) the heavy chain variable region of the antibody of the invention or functional derivatives thereof.

Preferably the ScFv fragment comprises a linker sequence between light chain and heavy chain variable regions. More preferably the ScFV fragment has essentially the sequence of SEQ ID No. 2.

It is a further object of the invention a synthetic or biotechnological derivative of the monoclonal antibody which comprises at least one region determining the complementarity of the antibody (CDR) and which is able to act as antagonist for the binding of NGF to TrkA. Preferably the region is within the variable region of the heavy chain, more preferably the region is comprised in the sequence from aa. 152 to aa. 276 of SEQ ID. No. 2.

It is within the scope of the present invention a nucleic acid encoding the antibody or derivatives thereof of the invention. Preferably the nucleic acid encodes the ScFv fragment of SEQ ID No. 2, more preferably the nucleic acid has the sequence of SEQ ID No. 1.

The nucleic acids of the invention can be advantageously used as transgenes to obtain non human transgenic animals, preferably mice, wherein the antibody is expressed in an inducible way, or under the control of promoters which determine the expression in the adult animal. These animals can be advantageously used to study and test drugs for human pathologies wherein the NGF/TrkA interaction is inhibited and, particularly, neurodegenerative pathologies. Transgenic non human animals can be obtained with standard techniques, i.e. as described in Allen et al., 1987.

Transgenic models (Smeyne et al., 1994) based on the repression of the TrkA gene show a lethal phenotype within 1-2 weeks from birth, and are then unsuitable to study TrkA in the adult and aged nervous system. Antibody expressing transgenic animals are disclosed by Piccioli et al., 1991, 1995.

It is within the scope of the present invention a phage or a prokaryotic vector comprising and able to express correctly and effectively the nucleic acid of the invention.

It is within the scope of the present invention a recombinant eukaryotic vector comprising and able to express correctly and effectively the nucleic acid of the invention, as well as a pharmacological composition comprising the recombinant vector for gene therapy of neurological pathologies. Pathologies comprise, but are not limited to, the following group: chronic pain, acute pain, neuromas, TrkA expressing neoplastic tumours.

It is within the scope of the present invention a pharmacological composition comprising an effective amount of the monoclonal antibody of the invention, or of synthetic and biotechnological derivatives thereof, able to recognise and bind to the high affinity tyrosine kinase receptor of NGF (Nerve Growth Factor), named as TrkA, and act as antagonist for the binding of NGF to TrkA, and a pharmaceutically acceptable carrier. The composition of the invention can be advantageously used for the treatment of neurological pathologies comprised, but not limited to, the following group: chronic pain, acute pain, neuromas, TrkA expressing neoplastic tumours.

In consideration of the fact that NGF may have some undesired collateral effects in therapy, the invention relates also to a pharmaceutical composition comprising pharmaceutically active amount of NGF and of the antibody or derivatives thereof according to the invention. Such composition should be able to inhibit at peripheral level the undesired effects of NGF.

It is a further object of the present invention engineered cells able to express the antibody of the invention or biotechnological and synthetic derivatives thereof, as well a pharmacological composition comprising said cells for gene therapy of neurological pathologies comprised but not limited to the following group: chronic pain, acute pain, neuromas, TrkA expressing neoplastic tumours.

In view of the specificity of the antibody of the invention and in the absence of undesired inducing effects, it can be advantageously used in a composition for in vivo "imaging" diagnostics.

The present invention will be described with reference to exemplifying, but not limiting, embodiments thereof. Reference will be done to the following Figures.

METHODS

Immunization Protocol

Balb/C 3T3 transfected cells, expressing $10^6$ human TrkA molecules per cell were used in a congenic immunization protocol. Three groups of female Balb/C mice were immunized with $10^5$, $5 \times 10^5$ and $10^6$ living cells per mouse, respectively. After five injections at two week intervals pre-fusion sera were tested for their ability to inhibit the binding of NGF to the TrkA receptor on TrkA+ Balb/C 3T3 cells. The greatest inhibition of NGF binding was found in the sera from mice injected with $5 \times 10^5$ cells (binding inhibition at a 1/100 dilution).

Hybridoma Production

Three days after a boost injection of TrkA+ Balb/C 3T3 cells, the mice were sacrificed, the spleens removed and splenocytes were fused to NSO myeloma (10:1 ratio) with polyethylene glycol (PEG 1500), as described (Novak et al., 1991). The hybridoma growth and selection were performed according to standard metohds (Galfre and Milstein, 1981).

Inhibition of $^{125}$I Binding to TrkA+ Balb/C 3T3 Cells 2.5 S NGF was purified from mouse submandibular glands and was iodinated to a specific activity of $10^5$ cpm/ng as described (Cattaneo et al. 1983). $5 \times 10^4$ TrkA+ Balb/C 3T3 cells were plated in each well of 96 well microplates in a volume of 50l of culture medium (DMEM with FCS 10%). Aliquots of 50 μl of hybridoma supernatant were incubated for 1 hour with cells, followed by the addition of the $^{125}$I-NGF solution ($5 \times 10^4$ cpm/well). The plates were processed as described (Cattaneo et al., 1988). Non specific binding was determined in parallel wells, in the presence of an excess (5 μg/ml) of unlabelled NGF. In parallel wells the binding was carried out in the presence of a non relevant hybridoma supernatant (Rab50) or of neutralizing anti-NGF (mAB αD11, Cattaneo et al., 1988).

ELISA

Soluble TrkA and TrkB receptors were engineered as immunoadhesins (Chamow and Ashkenazi, 1996) by linking the extracellular domain of the human TrkA receptor to the Fc portion of IgG2, constituted of a sequence of 35 amino acids, followed by CH2 and CH3 domains. The DNA sequences coding for the TrkA and TrkA immunoadhesins (TrkA-IgG and TrkB-IgG) were cloned into baculovirus (Autographa Califonica nuclear polyhedrosis virus, AcNPV) for expression in insect cells (Baculogold transfection kit, Pharmingen 1 ng.) and the proteins were purified by Protein A-Sepharose chromatography from serum free culture medium of High Five insect cells. For ELISA assay TrkA-IgG and TrkB-IgG were incubated at 2 μg/ml and then with 2 or 20 ng/ml of MNAC13 and anti mouse IgG, previously pre-absorbed on camel immunoglobulins.

Immunofluorescence Analysis

MNAC13 monoclonal antibody was purified from serum free hybrodoma supernatants by Protein A-Sepharose chromatography. $5 \times 10^4$ TrkA+ 3T3 Balb/C cells were incubated with MNAC13 purified antibody and analysed on an activated cell sorter (FACS). For immunofluorescence adherent cells were fixed with 3.7% paraformaldehyde in PBS, incubated with purified MNAC13, followed by FITC labelled anti mouse IgG and analysed by confocal microscopy (Olympus).

NGF Biological Assay with PC12 Cells

Rat. PC12 cells (Greene and Tischler, 1976) were cultured in RPMI with 10% heat inactivated horse serum and 5% FCS. For the bioassay the cells were transferred in serum free medium and incubated with 20 ng/ml NGF for 4 to 6 days, in the presence or in the absence of MNAC13 antibodies or of its single chain recombinant Fv version (scFvMNAC13). Alternatively the cells were incubate with 50 ng/ml of NGF for one week and then were mechanically removed from neurites for re-plating in the presence of 10 ng/ml of NGF and the addition of the appropriate antibody. The neurite growth was scored 24-48 hours later.

Intraventricular hybridoma Injections and Immunochemistry

Intraventricular hybridoma injection and analysis of the cholinergic phenotype of basal forebrain neurons were performed essentially as described (Molnar et al., 1997 and 1998). Briefly MNAC13 hybridoma cells and control myeloma cells (P3X63Ag8) cells were re-suspended in Hank (HBBS) solution at $2 \times 10^5$ cells/μl and injected into the right lateral ventricle of Wistar rats as described (Molnar et al., 1998). The injection was carried out at postnatal day 2 (P2) and the animals were sacrificed for analysis at P8 day. After perfusion under anaesthesia the brains were processed for aChAT immunohystochemstry as described (Molnar et al. 1997 and 1998). The level of MNAC13 antibodies in the cerebrospinal fluid (CSF) was determined by ELISA assay using soluble TrkA receptors as solid phase antigens.

For immunochemistry with MNAC13 the animals were anaesthetized with ether a perfused with PB (0.1 M, pH 7.4) followed by 4% paraformaldehyde/PB at 4° C. for 2 hours. After dissection the brains were fixed in 4% paraformaldehyde/PB at 4° C. for 2 hours, transferred in 25% sucrose/PBS, then frozen in isopentane at −20° C. and sectioned with a cryostat. The coronal sections containing the basal forebrain were collected on gelatinized slides and stored at −20° C. until processing. After blocking non specific binding in a solution of 10% FCS/5% BSA in Tris HCl 0.1M pH 7.4, 0.05% Triton-100 the sections were incubated overnight at 4° C. with anti-TrkA (6 μg/ml) in 10% FCS/2% BSA in Iris HCl 0.1M, pH 7.4, 0.05% Triton X-100. The next days the sections were incubated with anti-mouse IgG biotynilated for 2 hours at room temperature and for 1 hour in ABC kit (Vector). The reaction was developed in 3,3'-diaminobenzidine HCl. After dehydration the sections were mounted in DPX.

Cloning of the Variable Regions of mAb MNAC13.

The cloning of the variable regions of the mAb MNAC13 was carried out from hybridoma mRNA by variable region PCR. Variable region PCR was carried out with a set of oligonucleotide primers for mouse immunoglobulins (Krebber et al., 1997). The amplified VH and VK variable regions were assembled in a scFv format by PCR and cloned into pDNA vector (Bradbury et al., 1996). After finger printing analysis with BstNI restriction endonuclease, which confirmed a limited diversity of the resulting scFVs, phage particles displaying scFV fragments were subjected to ELISA using TrkA-IgG as solid phase antigen. The assay was developed with secondary HRP-coupled anti M13 antibodies. Positively identified phages were further assayed and finally used to produce soluble scFv fragments in *E. coli*. Bacterial supernatants were assayed by ELISA against TrkA-IgG, using a monoclonal antibody against SV5 tag (Hanke et al., 1992) present in the scFv fragment, followed by HRP-conjugated anti mouse IgG.

Results

Production and Characterization of a Monoclonal Antibody that Inhibits the Binding of NGF to TrkA In order to produce antibodies able to interfere with the neurotrophin binding activity of the TrkA receptor was used a congenic immunization protocol. Balb/C-3T3 cells expressing the human TrkA receptor produced by transfection of the human trk proto-oncogene were used for the immunization di Balb/C mouse. The number of cells was found to be critical for the induction of serum antibodies neutralizing NGF binding to target cells.

Figure 1:
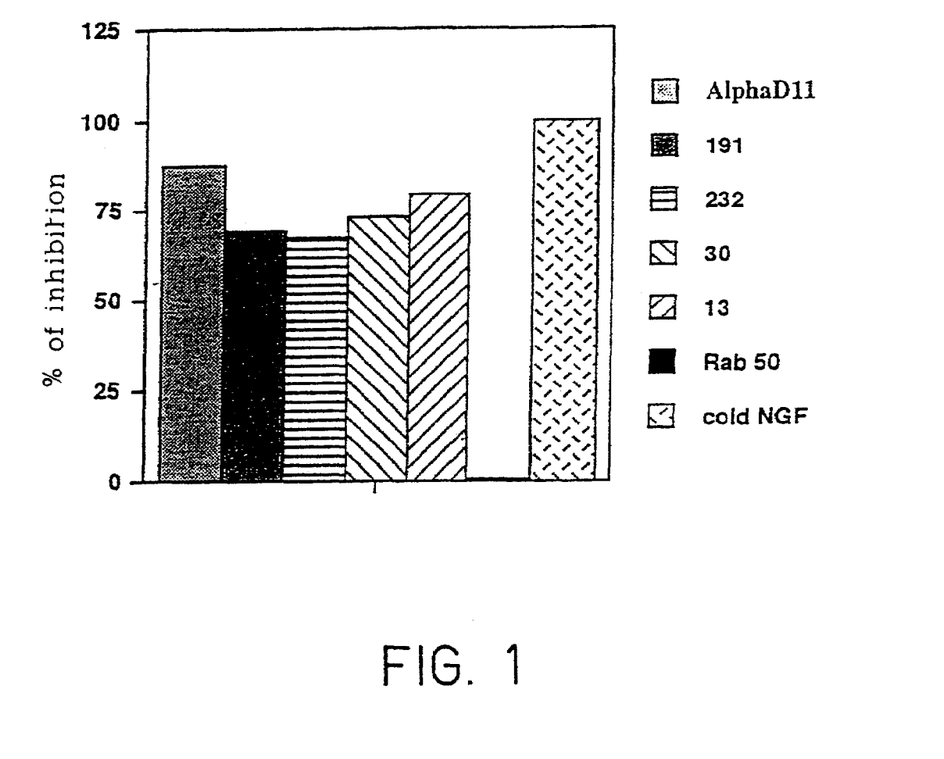
FIG. 1 Inhibition of binding of $^{125}$I-NGF to TrkA+ Balb/C 3T3 cells. Hybridoma supernatants were pre-incubated with TrkA+ Balb/C 3T3 cells, prior to the addition of $^{125}$I-NGF. The histogram reports the inhibition of specific binding NGF-cell by different antibodies. The specific binding was evaluated by subtracting from the total binding that obtained in the presence of an excess of unlabelled NGF. The values reported are the mean of triplicates.

The hybridoma supernatants were assayed for their ability in inhibiting the binding of $^{125}$I to 3T3-TrkA+ cells. Out of 1266 wells in which hybridoma growth was occurring only 4 showed a NGF neutralizing activity. The corresponding cells were subcloned obtaining MNAC13, C30, C191 and C232 clones. The ability of the antibodies produced by these clones to inhibit the binding of NGF to 3T3-TrkA+ cells is showed in FIG. 1. These anti-TrkA antibodies inhibit the binding of NGF as efficiently as the neutralizing anti-NGF αD11 antibody (FIG. 1). While the latter binds the active site of NGF the former binds the TrkA receptor, most likely at or near to the NGF recognising site. The IgG MNAC13 antibody was selected for further studies.

Figure 2:
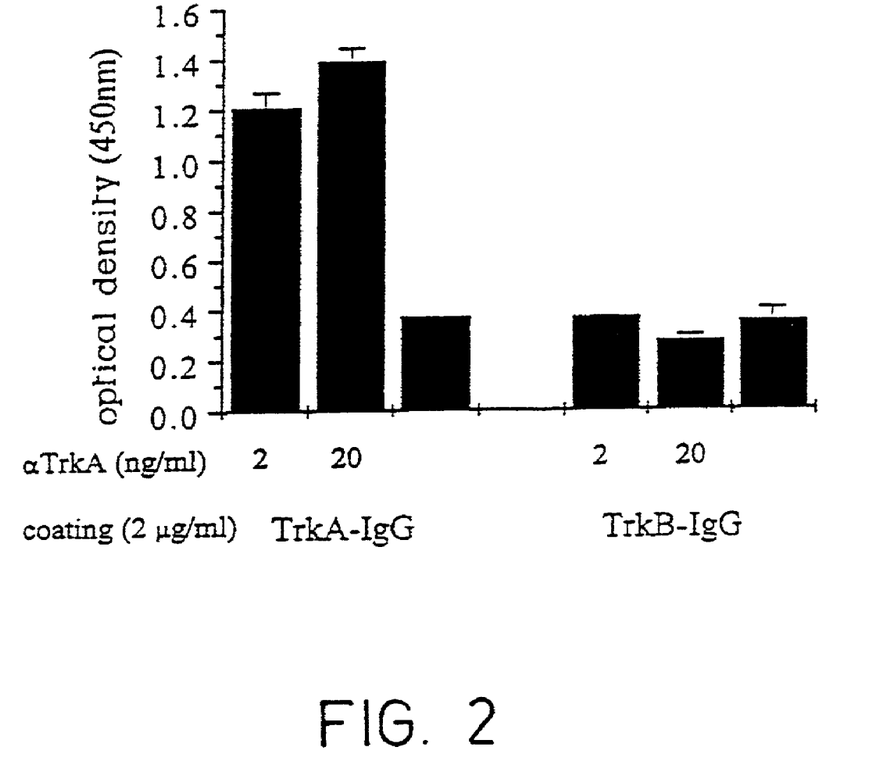
FIG. 2. MNAC13 recognises the extracellular domain of the TrkA receptor. Soluble TrkA and TrkB receptors, engineered as immunoadhesins, were used as solid phase antigens for an ELISA assay and incubated with 2 or 20 ng/ml of purified MNAC13 antibody.

The inhibition of NGF binding is obtained by a direct interaction of the antibodies with the extracellular portion of the TrkA receptor, as demonstrated by a variety of binding studies on a soluble form of human TrkA receptor, engineered as immunoadhesin (Chamow and Ashkenazi, 1996) in which the extracellular portion of the receptor is fused to the FC domains of the camel immunoglobulins (see Methods). FIG. 2 shows that MNAC13 antibody binds the TrkA immunoadhesin in an ELISA assay, while it does not react with TrkB immunoadhesin. This confirms that the MNAC13 antibody binds specifically to the extracellular portion of TrkA.

Figure 3:
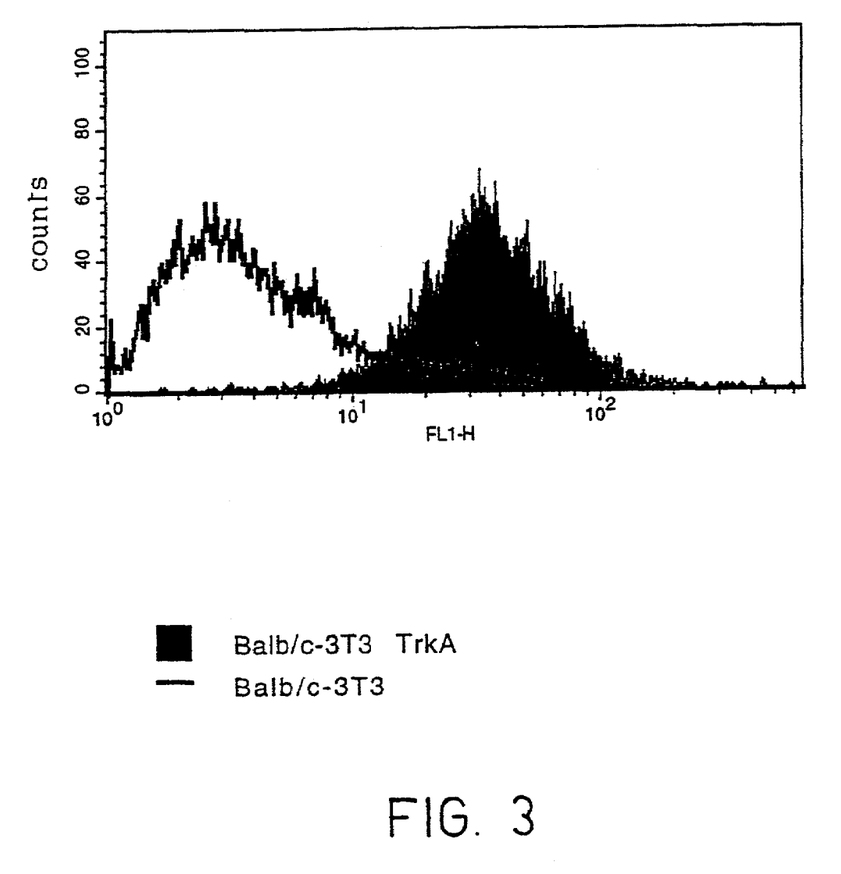
FIG. 3 MNAC13 recognises the TrkA receptor on living cells. Balb/C 3T3 or TrkA+ Balb/C 3T3 cells were incubated with MNAC13 antibody and subjected to FACS analysis.

FIG. 3 shows the result of a FACS analysis on 3T3 TrkA+ cells demonstrating that the MNAC13 antibody interacts with the human receptor expressed on the membrane of living cells. An immunofluorescence analysis confirms this result.

Figure 4:
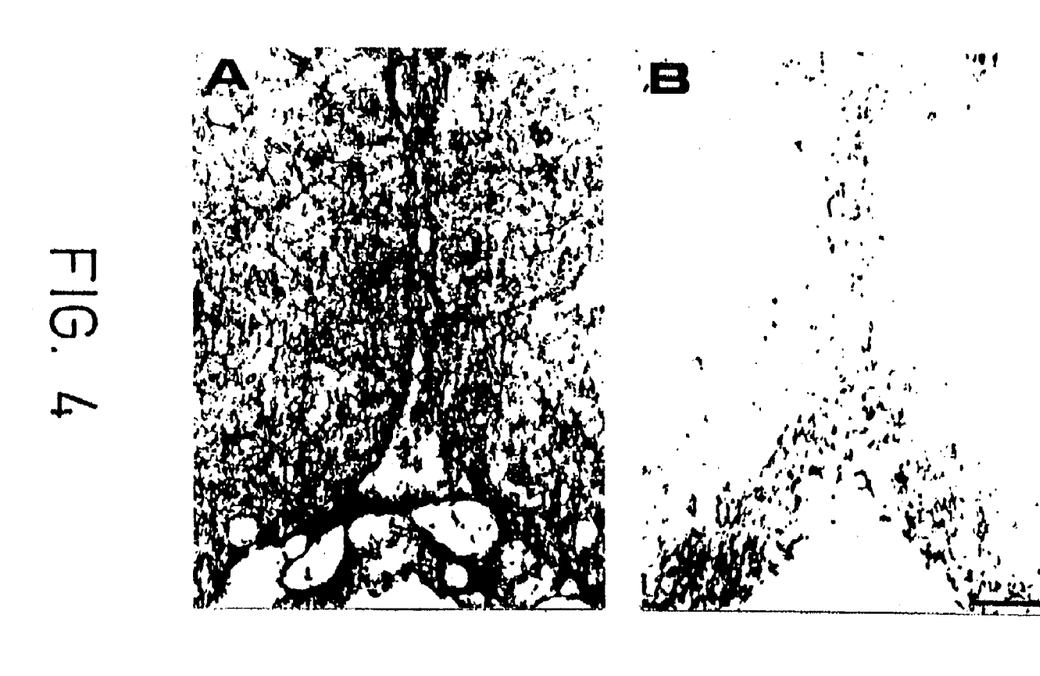
FIG. 4 MNAC13 labels the TrkA receptors on rat basal forebrain neurons. Coronal sections of P10 rat basal forebrain were incubated in the presence (A) or in the absence (B) of MNAC13 antibody. Scale bar: 98 μm.

The species specificity of MNAC13 antibodies was tested on the base of its ability to recognise TrkA receptors on rat neurons. Sections of rat brains were taken form the basal forebrain region (FIG. 4) which is rich in TrkA positive neurons. The intense staining obtained in the basal forebrain with MNAC13 antibody (FIG. 4A) shows that this antibody, obtained against the human TrkA receptor, recognises also its rat counterpart. The antibody does not stain brain regions such as the medial habenular nuclei, known to be lacking of positive TrkA neurons (Holtzmann et al., 1995).

Functional Block of TrkA-Mediated Biological Actions by MNAC13 Antibody

Figure 5:
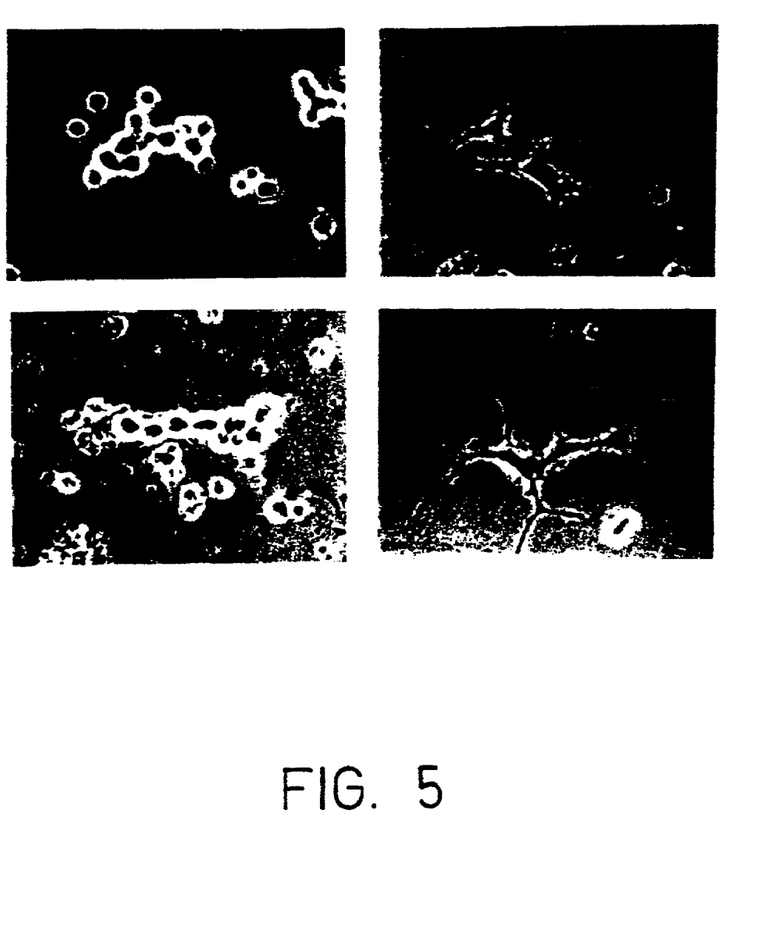
FIG. 5 MNAC13 inhibits the NGF induced differentiation of rat PC12 cells. PC12 cells were transferred to serum-free medium and incubated in the absence (A) or in the presence (B, C and D) of 20 ng/ml NGF for about 4 days. The MNAC13 antibody (4 μg/ml) inhibits completely NGF-induced survival and differentiation, while the control antibody 9E10 does not (D).
Figure 6:
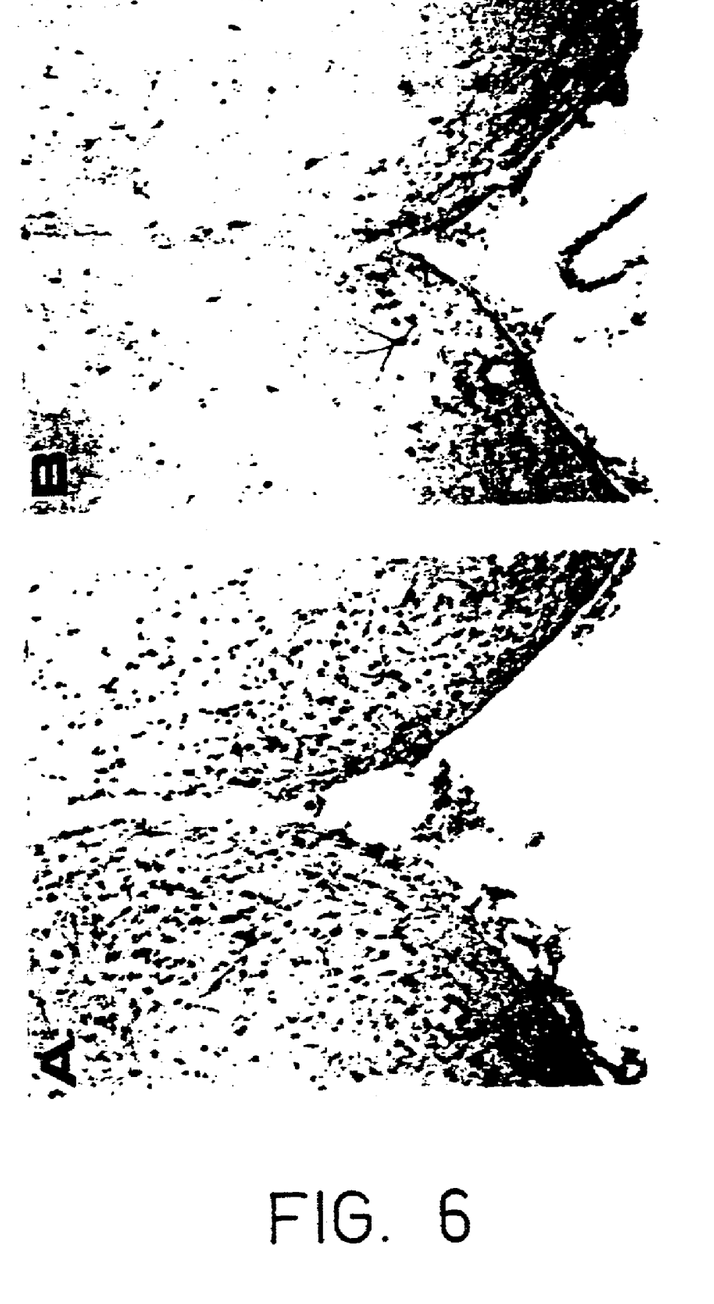
FIG. 6 Implant of MNAC13 secreting cells in the rat brain significantly reduces the number of cholinergic basal forebrain neurons. The cholinergic phenotype of P9 rat basal forebrain neurons was determined by immunoreactivity with the choline acetyltransferase (ChAT), further to intraventricular implant of MNAC13 ibridomas (B) of control myeloma (A) cells at P2 day. Note the marked reduction of the number of ChAT positive neurons in MNAC13 implanted rats (B). Scale bar. 65 μm.

The ability of MNAC13 antibody to inhibit in vivo the biological activation of the TrkA receptor by the NGF ligand was therefore studied in PC12 cells in vitro (FIG. 5) as well as in vivo (FIG. 6).

The NGF-induced differentiation of PC12 cells (FIG. 5B) is completely inhibited by incubation of the cultures with MNAC13 antibody (FIG. 5C), as compared to incubation with a non relevant antibody (FIG. 5D).

The cholinergic neurons of the basal forebrain are a well known target for NGF action in the central nervous system (Korsching, 1986; Holtzman et al., 1992). The hybridoma cells secreting the MNAC13 antibody were implanted in the lateral ventricle of neonatal rats two days after birth and the cholinergic phenotype of the neurons was studied a week (P9) later by immunohistochemistry with antibodies against cholineacetyltransferase (ChAT). This experimental approach has been used recently to study the effects of implanted cells secreting the anti-NGF monoclonal antibody αD11 (Berardi et al., 1994; Molnar et al., 1997 and 1998). One week after the implant the level of anti-TrkA antibodies found in the cerebrospinal fluid, determined by ELISA, was of 1.4 ng/μl. The results in FIG. 6 show that the number of ChAT positive cells is dramatically reduced in the brains implanted with the anti-TrkA antibody with respect to the controls (injected with a non relevant myeloma). A quantitative evaluation of the number of the positive ChAT neurons showed that this number is reduced by 70% in the medial septum and by 77% in the diagonal band of rats implanted with MNAC13 antibody, with respect to the controls. An extension of this study to various post-natal ages, comparing the effects obtained in a previous study, with implant of cells secreting an anti-NGF neutralizing antibody (Molnar et al., 1997, 1998) showed that the deprivation effects of the cholinergic system of the basal forebrain obtained with the anti-TrkA MNAC13 antibody are much more severe.

Isolation of a Recombinant Functional Form of mAb MNAC13 with a Significantly Reduced Size In order to expand the range of application the variable regions of this antibody were cloned and engineered into a recombinant antibody of smaller size.

The cloning of the variable regions of monoclonal antibodies from the corresponding hybridoma can be complicated leading to the cloning of artifactual variable regions. Therefore the author used the technique according to Winter et al. (1994). The variable heavy (VH) and light (VL) regions of the MNAC13 antibody were amplified by PCR from a cDNA derived from hybridoma mRNA using mouse IgG specific oligonucleotide primers. The variable regions were assembled into single chain Fv (scFv) by PCR and cloned into pDAN vector to allow the expression of antibody fragments cloned on the surface of filamentous phage. ScFv fragments represents a biotechnological derivative of the original antibody (Bird et al., 1988) and consist of the variable light and heavy regions joined to a linker peptide which links the C terminus of the VL region to the N terminus of the VH region. The nucleotide sequence of ScMNAC13 specific fragment is showed in SEQ ID No. 1. The amino acid sequence is showed in SEQ ID No. 2 in which the VL region is from aa. 23 to aa. 134, the VH region is from aa. 152 to aa. 276.

The CDRs (regions determining the antibody complementarity) are three for each chain, and particularly:
  VL CDR1 aa. 46-55 of SEQ ID No. 2;
  VL CDR2 aa. 71-77 of SEQ ID No.2;
  VL CDR3 aa. 1104119 of SEQ ID No. 2;

VH CDR1 aa. 176-185 of SEQ ID No. 2;
VH CDR2 aa. 200-216 of SEQ ID No. 2;
VH CDR3 aa. 240-262 of SEQ ID No. 2.

The sequence of the light and heavy variable regions of the MNAC13 antibody was compared to that of the antibody described in patent application PCT No. WO97/21732, as showed in Tables 1 and 2.

TABLE 1

Alignment of the light chain of 5C3 and MNAC13

```
                                                      38
              DILQTQSPAILSASPGEKVTMTCRASSSVSYMHWYQQK
              ||||||||||||||||||
MKYLLPTAAAGLLLLAASGAHADIVLSQSPAIMSASLGEEITLTCSASSSVSYMHWYQQK
                                                      60

98
PGSSPKPWIYATSNLASGVPARFSGSGSGTSYSLTISRVEAEDAATYYCQQWSSNPLTFG
||||||||||  |||||||||  ||||||  |||||||      ||||
SGTSPKLLIYTTSNLASGVPSRFSGSGSGTFYSLTISSVEAEDAADYYCHQWSSYPWTFG
                                                     120

105
AGTKLEI
 ||||||
GGTKLEIKRSGGST
        134
```

TABLE 2

Alignment of the heavy chain of 5C3 and MNAC13

```
                                                       54
      VQLQESGTVLARPVGASVKMSCKASGYTFTSYWMHWVKQRPGQGLEWIGAIYPG
       |||                |||                |||
SSSGTEVKLMESGGGLVQPGGSLKLCSA-ASGFTFSTYTMSWARQTPEKRLEWVAYISKG
                                                       59

111
DSDTSYNQKFKGEAKLTAVTSTSTAYMELSSLTNEDSAVYYCTL---YGNYESYYAMDYW
               |||           |||      |||           ||||
GGSTYYPDTVKGRFTISRDNAKNTLYLQMSSLKSEDTALYYCARGAMYGNDFFYP-MDYW
                                                      118

121
GQGILSHRLL
|||
GQGTSVTVSSASG
        131
```

Figure 7:
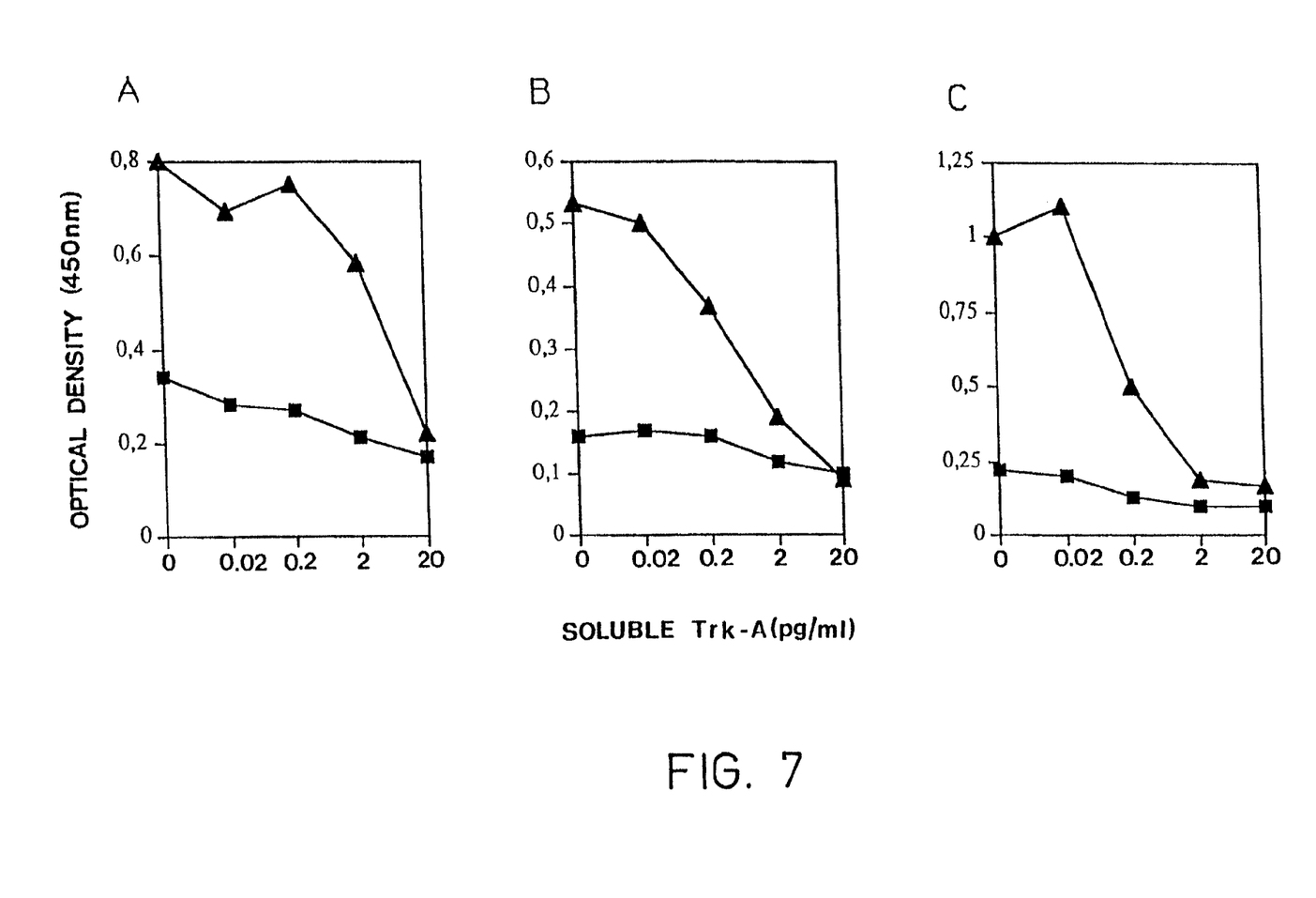
FIG. 7 Recombinant forms of MNAC13 mAB bind TrkA. Phages with scFvMNAC13 (A), soluble scFvMNAC13 (B) and the parental monoclonal antibody MNAC13 (C) were used in an ELISA assay using TrkA immunoadhesin as solid phase antigen in the presence of increasing concentrations of competing soluble TrkA-immunoadhesin. ■: ten-fold dilution of the antibody with respect to ▲.

The PCR assembled ScFV fragments were expressed on the filamentous phage, as fusion to the p3 phage protein. The minilibrary of phage particles was screened by an ELISA assay on phages using the TrkA immunoadhesin as solid phase antigen. This led to the isolation of positive phages which express on their surface the ScFv version of the MNAC13 parental antibody (scFvMNAC13). The binding properties of this phage, as well as those of the scFv soluble fragment derived form this phage were characterized by a competition ELISA assay (FIG. 7). The TrkA immunoadhesin was coupled in solid phase and incubated with MNAC13 expressing phage particles (FIG. 7A), with ScFvMNAC13 soluble antibody (FIG. 7B) or with parental MNAC13 antibody (FIG. 7C), in the presence of increasing amounts of competing soluble TrkA immunoadhesin. The results confirm the ScFv version of the parental monoclonal antibody either on phage or secreted by E. coli binds TrkA as efficiently as the parental monoclonal antibody.

Figure 8:
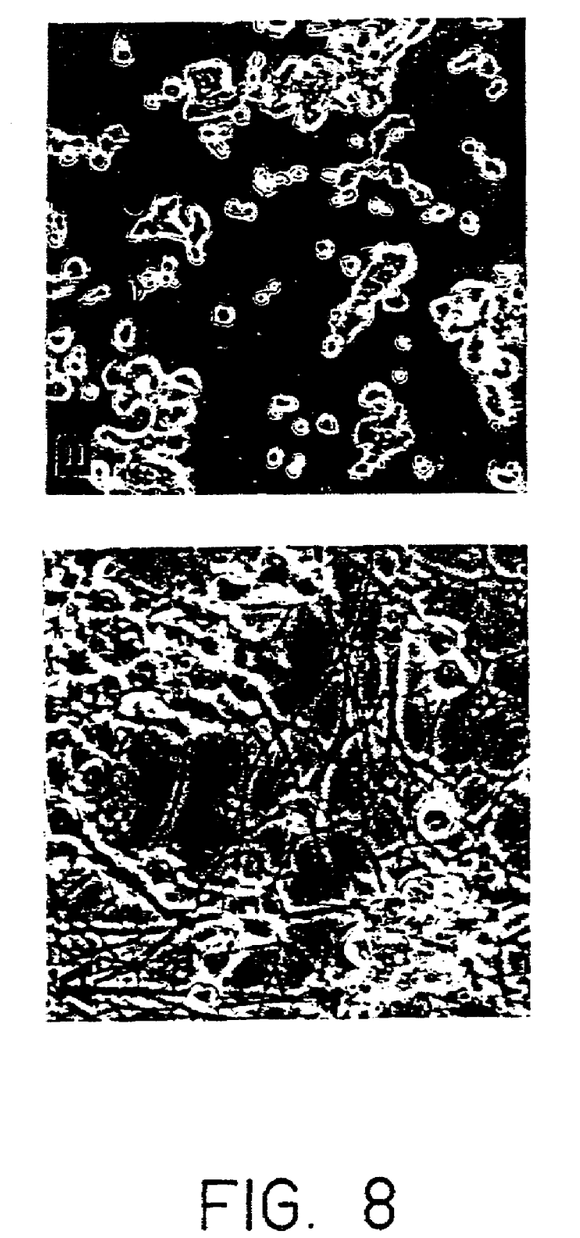
FIG. 8. Inhibition of NGF-induced neurite growth of PC12 cells by the recombinant antibody ScFvMNAC13. Periplasmic fraction containing the recombinant ScFvMNAC13 (B) or ScFv control fragment (antifox ScFv) were added, together with 10 ng/ml of NGF to PC12 cells induced for 7 days with 50 ng/ml of NGF and plated again at the beginning of the assay. The recombinant ScFvMNAC13 antibody in B inhibits the re-growth of neurites in replated NGF induced PC12 cells, mediated by the activation of TrkA by NGF.

The biological activity of ScFVMNAC13 was tested on PC12 cells. The cells were incubated for one week with 50 ng/ml of NGF, after which they were replated in the presence of NGF and the antibody ScFVMNAC13 fragment. As shown in FIG. 8 ScFVMNAC13 fragment inhibits dramatically the extension of neurites from PC12 cells, confirming that the recombinant single chain Fv of the MNAC13 antibody retains the neutralization properties of the parental antibody. The small size of this single polypeptide antibody expands the range of applications of the antibody of the invention facilitating its delivery and expression within the nervous tissue.

Nociception Test

The MNAC13 antibody was used in a nociception test for determination of the pain sensitivity by "hot plate test". The experiment was carried out according to McMahon et al. (1995), using the antibody MNAC13 as immunoadhesin. The antibody was infused subcutaneously into hind paw of an adult rat for a period of three weeks or by an osmotic minipump. The nociception sensitivity was evaluated at intervals using hot plate test (Eddy and Leimbach, 1953), which mimics hyperalgesia situations following inflammation or partial damage to the nerve. The nociceptive stimulus induces in such a case a response (paw licking and/or jumping) which presumes an integrated coordination higher than simple reflex. According to the test the animal is put in a pen having a plate heated to the desired temperature as base, usually 56°. The latency of any of two responses (paw licking and jumping) is measured in control animals (treated with non relevant antibody) and in those treated with anti-TrkA antibody. The result of the experiment demonstrated the occurrence of a remarkable hypoalgesia, as pointed out by a significant increase of the latency in the MNAC13 treated group.

BIBLIOGRAPHY

Allen, N. D., et al. (1987). In Mammalian development: A practical approach, M. Monk, ed. (Washington D.C.: IRL Press) pp 217-234.
Anand et al. (1996) Nature Medicine 2, 703-707.
Barde Y A (1994) J. Neurobiol 25, 1329-1333
Berardi N. et al. (1994) Proc. Natl. Acad. Sci USA 91:684-688
Bird R E, et al. (1988) Science 242:423-425.
Bradbury A, Cattaneo A, Hoogenboom H (1996) In: Manual of the EMBO theoretical and practical Course, pp. 1-122, Trieste 18-26 November
Cattaneo A, et al. (1983) Eur. J. Biochem. 135:285-290.
Cattaneo A, Rapposelli B, Calissano P (1988), J. Neurochem 50:1003-1010.
Chamow S M, Ashkenazi A (1996), Trends in Biotechnol 14:52-60.
Ebendal T, et al. (1991) In: Plasticity and regeneration in the nervous system (Timiras P., Privat A, eds.), New York: Plenum Press
Eddy N B and Leimbach D J (1953) J. Phar. Exp. Ther. 107:385-393.
Galfrè G. Milstein C (1981) Methods Enzymol. 73:3-45.
Greene L A, Tischler A S (1976) Proc. Natl. Acad. Sci. Usa 73:2424-2428.
Hanke T, Szawlowski P, Randall R E (1992) J. Gen. Virol. 73:653-60.
Holtzman D M, et al. (1992) Neurin. 9:465-478.
Holtzman D M, et al. (1995) J. Neuroscience 15:1567-1576.
Jones P T, et al. (1986) Nature 321:522-525.
Kaplan D R et al. (1991) Science 252:554-558.
Klein R, et al. (1991) Cell 65:189-197.
Korsching S (1986) Trends in Neurosci 9:570-573.
Krebber A, et al. (1997) J. Immunol. Methods 15:35-55.
Kramer K, et al. (1997) Eur. J. Cancer 33:2090-2091.
Indo et al. (1996) Nature Genetics 13, 485-488.
LeSauter L. et al. (1995) J. Biol. Chem. 270:6564-6569.
LeSauter L., et al. (1996) J. Neurosci. 16, 1308-1316.
Levi-Montalcini R (1987) EMBO J 6, 1145-1316.
Levi-Montalcini R, Angeletti P U (1996) Pharmacol. Rev. 18:619-628.
Levine I D (1998) Neuron 20:649-654.
Lindsay R M et al. (1994) Trends in Neuroscience, 17, 182.
McMahon et al. (1995) Nature Medicine 1, 774-780.
Molnar M. et al. (1997) NeuroReport 8:575-579
Molnar M. et al. (1998) Eur. J. Neurosci. 10: 3127-3140.
Novak M. et al. (1991) Proc. Natl. Acad. Sci. USA 88:5837-5841
Piccioli P. Et al. (1991) Proc. Natl. Acad. Sci. USA 88:5611-5615.
Piccioli P. Et al. (1995) Neuron 15:373-384.
Smeyne R J, et al. (1994) Nature 368:246-249.
Sinder W D, McMahon S B (1998) Neuron 20:629-632.
Torcia M, et al. (1996) Cell 85:345-356.
Vaughan T J, Osbourne J K, Tempest P R (1998) Nature Biotech 16, 535-539.
Verge V M K, et al. (1992) J. Neurosci. 12:4011-4022.
Winter G, et al. (1994) Annu. Rev. Immunol. 12:433-455.
Wood (1996) Nature Genetics 13, 382-383.

The invention claimed is:

1. A monoclonal antibody or antigen binding fragment thereof, wherein said antibody or antigen binding fragment thereof is able to bind TrkA, wherein said antibody or antigen binding fragment thereof inhibits the functional activation of TrkA, and wherein the variable region of the light chain of said antibody or antigen binding fragment comprises the sequence from aa. 23 to aa. 134 of SEQ ID NO: 2.

2. The monoclonal antibody or antigen binding fragment thereof according to claim 1 wherein the variable region of the heavy chain comprises the sequence from aa. 152 to aa. 276 of SEQ ID NO: 2.

3. A monoclonal antibody or antigen binding fragment thereof, wherein said antibody or antigen binding fragment thereof is able to bind TrkA, wherein said antibody or antigen binding fragment thereof inhibits the functional activation of TrkA, and wherein the variable region of the heavy chain of said antibody or antigen binding fragment comprises the sequence from aa. 152 to aa. 276 of SEQ ID NO: 2.

4. The monoclonal antibody or antigen binding fragment thereof of claim 1 or 3, wherein said antigen binding fragment is an scFv fragment or Fab fragment.

5. The monoclonal antibody or antigen binding fragment thereof of claim 4, wherein said ScFv or Fab fragment comprises a linker sequence between the variable region of the light chain and the variable region of the heavy chain.

6. The monoclonal antibody or antigen binding fragment thereof of claim 5, wherein said ScFv fragment has the sequence of SEQ ID NO: 2.

7. A monoclonal antibody or scFv or Fab fragment thereof, wherein said monoclonal antibody or scFv or Fab fragment binds TrkA, said monoclonal antibody or scFv or Fab fragment thereof comprising a light chain variable domain comprising a CDR1, CDR2, and CDR3 region, wherein said CDR1 comprises aa. 46-55 of SEQ ID NO: 2, CDR2 comprises aa. 71-77 of SEQ ID NO: 2, and CDR3 comprises aa. 110-119 of SEQ ID NO: 2 and a heavy chain variable domain comprising a CDR1, CDR2, and CDR3 region, wherein said CDR1 comprises aa. 176-185 of SEQ ID NO: 2, CDR2 comprises aa. 200-216 of SEQ ID NO: 2, and CDR3 comprises aa. 249-262 of SEQ ID NO: 2.

8. A pharmaceutical composition comprising the antibody or scFv or Fab fragment thereof according to claim 7, and a pharmaceutically acceptable carrier.

9. A monoclonal antibody or antigen binding fragment thereof, wherein said monoclonal antibody or antigen binding fragment thereof binds TrkA, said monoclonal antibody or antigen binding fragment thereof comprising a light chain variable domain comprising a CDR1, CDR2, and CDR3 region, wherein said CDR1 comprises aa. 46-55 of SEQ ID NO: 2, CDR2 comprises aa. 71-77 of SEQ ID NO: 2, and CDR3 comprises aa. 110-119 of SEQ ID NO: 2, and further comprising a heavy chain variable domain comprising a CDR1, CDR2, and CDR3 region, wherein said CDR1 comprises aa. 176-185 of SEQ ID NO: 2, CDR2 comprises aa. 200-216 of SEQ ID NO: 2, and CDR3 comprises aa. 249-262 of SEQ ID NO: 2.

10. A pharmaceutical composition comprising the antibody or antigen binding fragment thereof according to claim 9, and a pharmaceutically acceptable carrier.

11. A monoclonal antibody or antigen binding fragment thereof, wherein said antibody or fragment thereof is able to bind TrkA, wherein the variable region of the light chain of said antibody or antigen binding fragment comprises the sequence from aa. 23 to aa. 134 of SEQ ID NO: 2 and the variable region of the heavy chain comprises of the sequence from aa. 152 to aa. 276 of SEQ ID NO: 2.

12. A pharmaceutical composition comprising the antibody or antigen binding fragment thereof according to claim 11, and a pharmaceutically acceptable carrier.

* * * * *